United States Patent [19]

McGregor et al.

[11] Patent Number: 4,660,559
[45] Date of Patent: Apr. 28, 1987

[54] STERILE SURGICAL NEEDLES WITH A HARD SHARP CUTTING EDGE AND METHOD FOR PRODUCING THE SAME

[75] Inventors: Walter McGregor, Flemington; Lee Bendel, Lebanon, both of N.J.

[73] Assignee: Ethicon, Inc., Somerville, N.J.

[21] Appl. No.: 533,471

[22] Filed: Sep. 19, 1983

[51] Int. Cl.[4] ............................................. A61B 17/06
[52] U.S. Cl. .................................................. 128/339
[58] Field of Search ...................... 128/339; 148/39, 4; 30/350, 346.54

[56] References Cited

U.S. PATENT DOCUMENTS

| 3,411,208 | 11/1968 | Malm | 148/39 |
| 3,875,946 | 4/1975 | Duncan | 128/339 |
| 4,128,351 | 12/1978 | Kurtz et al. | 128/339 |
| 4,151,014 | 4/1979 | Charschan et al. | 148/39 |

Primary Examiner—Robert P. Swiatek
Assistant Examiner—Cary E. Stone
Attorney, Agent, or Firm—Robert L. Minier

[57] ABSTRACT

A unitary sterile surgical needle having a hardened cutting edge and a malleable center portion and body section.

6 Claims, 20 Drawing Figures

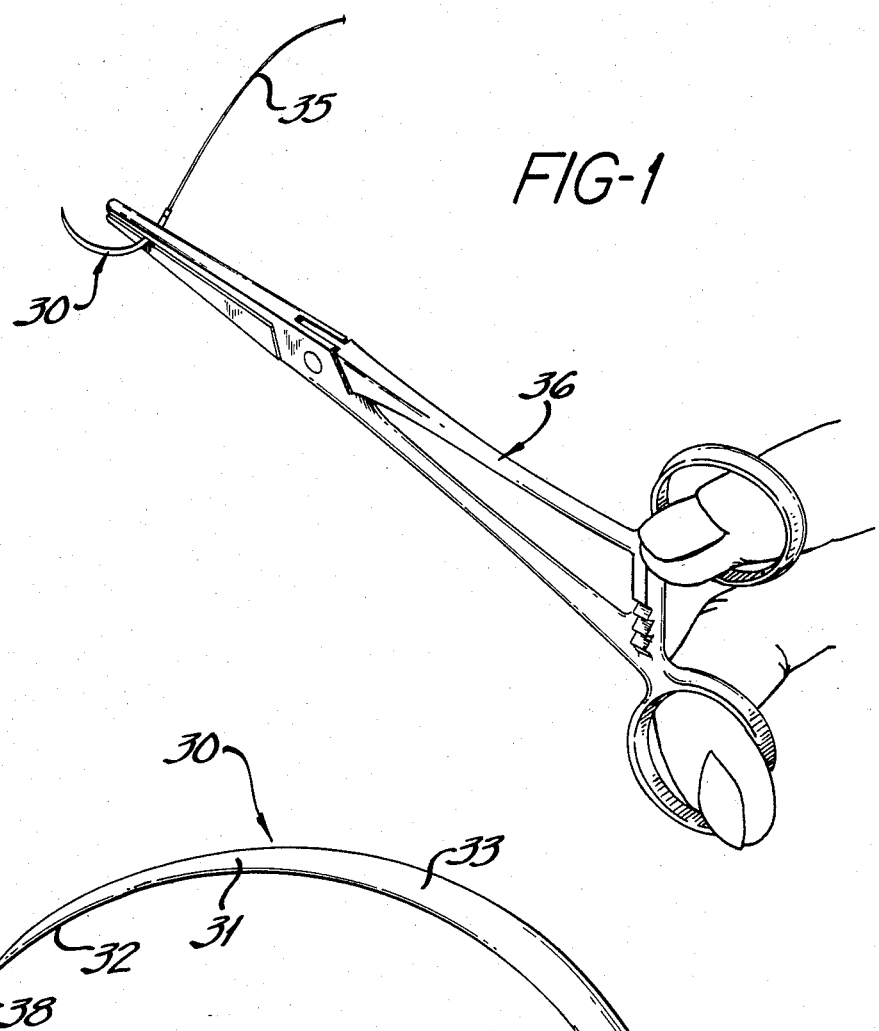
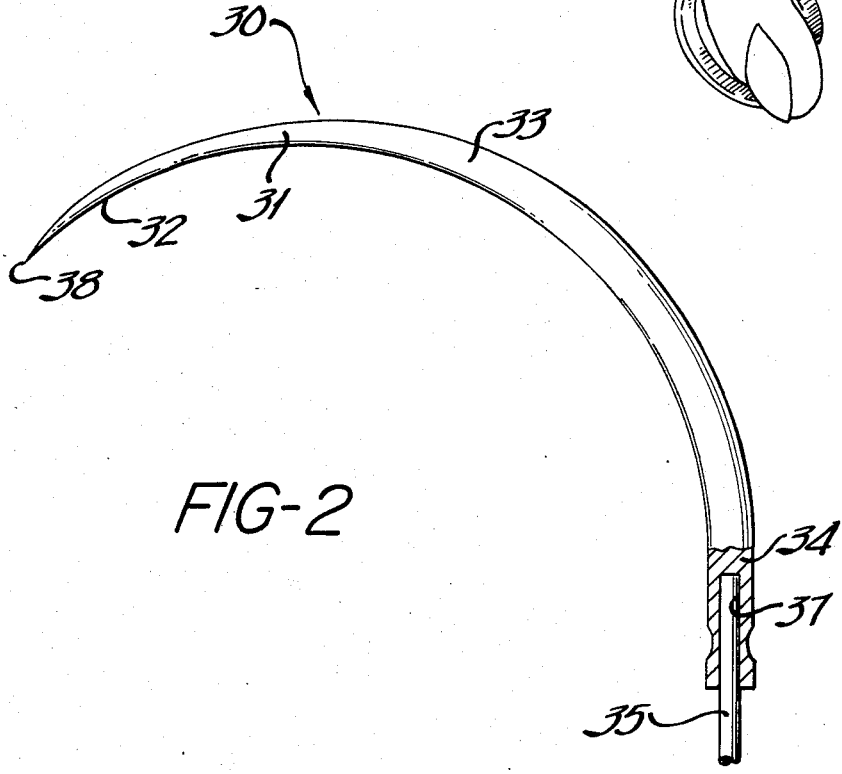

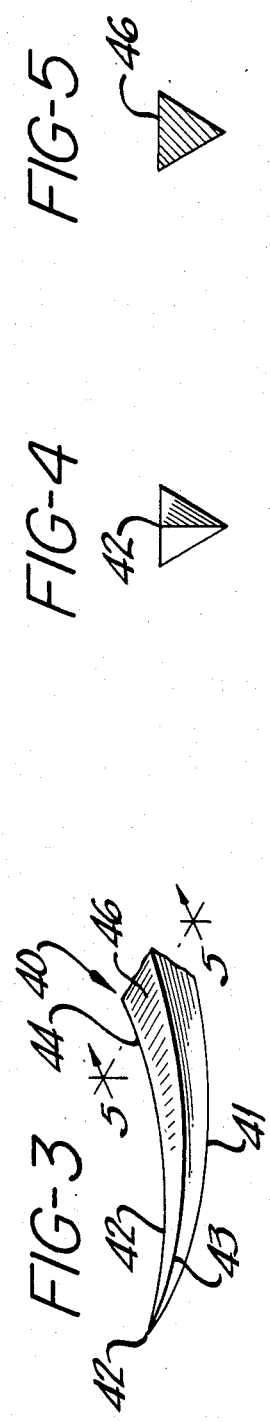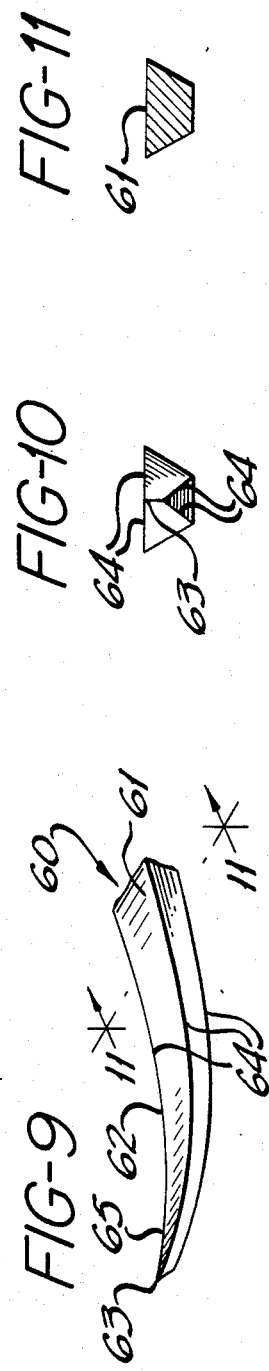

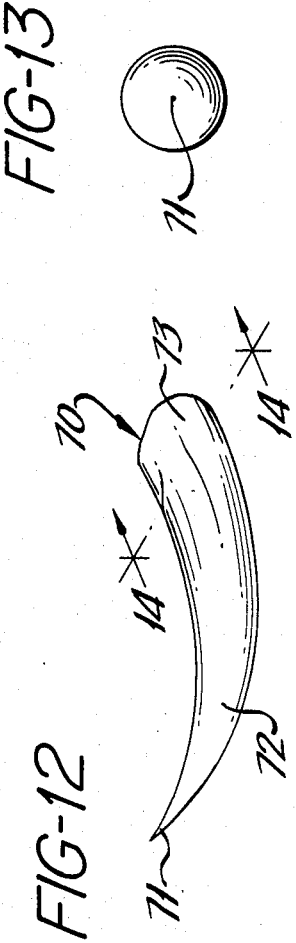

STERILE SURGICAL NEEDLES WITH A HARD SHARP CUTTING EDGE AND METHOD FOR PRODUCING THE SAME

Surgical needles have been known for some time and such needles with sutures attached are commonly used in various types of surgical procedures. The surgical needles are usually made from stainless steel and have a blunt end to which a suture is attached. The blunt end may be drilled or have a channel placed therein and the suture is usually swaged or crimped in the drilled hole or channel. In order to reduce trauma in placing sutures in tissue, the suture itself generally has a diameter no greater than the diameter of the needle. Also, the point and cutting edge of the needle should be made as sharp as possible so as to provide the least amount of force required to penetrate the tissue and place the suture and consequently cause the least amount of trauma to the sutured area.

Most surgical needles are curved; that is, they have the shape of some part of a circle. This may be from a quarter of a circle to two-thirds of a circle. At one end of the needle is the point or the extreme tip of the needle. The section from that extreme point to the maximum width of the needle is termed the "blade" of the needle. In cutting needles, the blade includes the cutting edge from the point towards the blunt end. Behind the cutting edge is the body portion of the needle; that is, the area of the needle to be grasped by an appropriate needle holder which in turn is used to place the needle. At the blunt end of the needle is the swage or the portion of the needle into which the suture is inserted and affixed.

In placing the needle, the needle is grasped by a suitable needle holder; that is, a forceps type instrument that grasps the needle at the body portion with sufficient force to insure that the needle will not move or turn in the instrument when the needle is being placed by the surgeon. This means the body portion of the needle should be relatively malleable and not brittle. If the body is too brittle it may break during use if too much force is placed on the needle by the instrument or during the placement. The cutting edge and the point of the needle should be as sharp as possible. The harder the needle the sharper it can be made. The sharper the needle, the less force required to make the initial preparation and the less the drag by the needle body during the remainder of the passage of the needle through tissue. Generally speaking, to make a sharp needle you need a very hard metal; however, the harder the metal the more brittle it becomes and the greater the chance it will be broken by the needle holding instrument or during placement. Various attempts have been made to improve the combination of characteristics of having a very hard and sharp cutting edge and a relatively malleable, non-brittle, body portion that will not break when extreme force is placed on it by the needle holder and a stable non-brittle body portion to prevent movement of the needle within the needle holder. One such technique is to flatten the body portion or even place ribs along the body portion to improve the stability of the needle in the needle holder.

Surgical needles generally come in sizes from small to very small to microscopic; i.e., not readily visable with the naked eye but requiring some type of magnification to see. Generally, the larger surgical needles are from 1 to 3 inches in length and have a diameter of from about 0.039 to 0.060 inches. Because of the small size of surgical needles, to our knowledge, nobody to date has been able to produce a needle having different properties in different portions of the needle. In the prior art needles, there is generally a compromise between the hardness of the needle for the sharpness and the malleability of the needle to prevent breaking. Nobody has been able to make one portion of the needle very malleable and non-brittle while making another portion of the needle extremely hard and hence able to be made very sharp.

Heat treating of needles has been known for some time and most surgical needles are treated or tempered to give the maximum desirable combination of hardness and malleability. Lasers also have been known for some time and lasers or electron beams have been successfully used in selective surface hardening of many various products. An excellent review of surface treatments to convert specific properties on materials is given in the Dec. 19, 1979, issue of *Metallic Materials Technology*, Book 11 (12), pps, 685–691. Generally, what is accomplished is the material or work piece to be treated is coated with a substance which increases its absorbitivity and the work piece impinged by the laser beam at high power densities. The beam is removed and the material allowed to cool sufficiently fast to develop the desired heat treating. The critical powers are the power density and the energy profile of the beam. Another technique is to use an electron beam and in this method, heat is applied to the surface of the piece to be treated by a stream of high energy electrons. A heated filament is used as the electron emitter and an anode accelerates the electrons through a high voltage potential. A focus coil concentrates the beam at an adjustable distance and a deflection coil is used to move the beam as desired. This technique is usually carried out under vacuum and the beam is allowed to rapidly traverse the area to be hardened. Both the laser and the electron beam techniques have been used to surface harden various types of metal work pieces. Also, the laser technique has been used to deburn or remove flash from metal pieces. By directing and focusing a suitable laser beam at the edges of a metal piece, the flash or burring on that metal piece may be vaporized and removed from the piece.

What we have discovered is that by directing an appropriate laser beam or electron beam at the cutting edge of a surgical needle, we can attain a very hard edge which may then be ground to form an extremely sharp edge. Unexpectedly, we are able to accomplish this without causing undue brittleness in the body of the needle and even more unexpectedly without causing undue brittless in the center portion of the needle at the cutting edge portion. Our new sterile needles may be made with extremely sharp cutting edges while having a very malleable and ductile body portion which has considerable resistance to bending or breaking caused by undue stresses placed on the body portion by the needle holding instrument.

SUMMARY OF THE PRESENT INVENTION

What we have discovered is a sterile surgical needle that has a cutting section having a point, an internal center portion and at least one cutting edge. The point and cutting edge provide for penetration and ease of passage through tissue. The needle also comprises a body section which provides for handling and manipulation of the needle to allow for placement of a suture attached to the needle. The cutting edge has a surface hardness of at least 45 and preferably 48 or more measured on the Rockwell C Hardness Scale and the internal center portion and the body section of the needle are malleable and resistant to breaking. By "malleable" it is meant that the center portion and the body section of the needle are not as hard as the cutting edge.

The new and improved surgical needles of the present invention are produced by forming a cutting edge at one end of a piece of steel wire. The edge is treated with a laser beam to harden the edge to a depth of from about 0.0001 inch to 0.010 inch to a hardness of at least 45 and preferably 48 or more as measured on the Rockwell C Hardness Scale. The hardened edge is ground to sharpen the edge and form a sharp cutting edge and the needle is shaped to the desired shape for use in surgery.

BRIEF DESCRIPTION OF THE DRAWING

FIG. 1 is a perspective view of a sterile surgical needle in accordance with the present invention having a suture swaged to the blunt end with the needle held in a forceps type needle holding instrument;

FIG. 2 is an enlarged side view of a sterile surgical needle according to the present invention with a suture swaged to the blunt end;

FIG. 3 is an enlarged perspective view of one embodiment of the needle of the present invention;

FIG. 4 is a front view of the point of the needle depicted in FIG. 3;

FIG. 5 is a cross-sectional view taken along line 5—5 of FIG. 3;

FIG. 6 is an enlarged perspective view of a portion of another embodiment of a sterile surgical needle according to the present invention;

FIG. 7 is a front view depicting the point of the needle shown in FIG. 6;

FIG. 8 is a cross-sectional view taken along line 8—8 of FIG. 6;

FIG. 9 is an enlarged perspective view of another embodiment of a sterile surgical needle according to the present invention;

FIG. 10 is a front view depicting the point of the needle shown in FIG. 9;

FIG. 11 is a cross-sectional view taken along line 11—11 of FIG. 9;

FIG. 12 is an enlarged perspective view of yet another embodiment of a sterile surgical needle according to the present invention;

FIG. 13 is a front view of the point of the needle depicted in FIG. 12;

FIG. 14 cross-sectional view taken along line 14—14 of FIG. 12;

FIG. 15 is an enlarged perspective view of yet another embodiment of a sterile surgical needle according to the present invention;

FIG. 16 is a front view depicting the point of the needle shown in FIG. 15;

FIG. 17 is a cross-sectional view taken along line 17—17 of FIG. 15;

DESCRIPTION OF THE DRAWING

Figure 20:
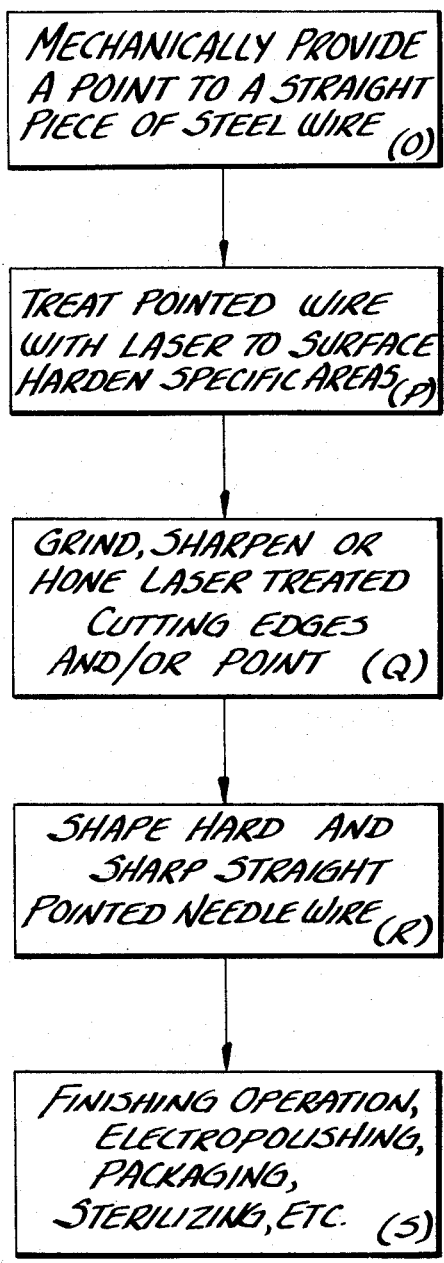
FIG. 20 is a schematic diagram depicting the steps for producing a very sharp needle.

Referring to FIG. 1 there is shown a sterile surgical needle 30 according to the present invention. As depicted in FIG. 2 the needle has a cutting section 31 having a cutting edge 32, a body portion 33 and a blunt end 34 with an appropriate suture 35 swaged into the blunt end. The body portion of the needle is clamped and locked in a forceps type needle holding instrument 36. The instrument places considerable force on the body of the needle. It is critical that the needle be held so that there is no lateral movement, transverse movement, or rotational movement in the needle holding instrument and, hence, it is important to place sufficient force on the body of the needle so that it is adequately locked in the instrument.

As more clearly shown in FIG. 2, the suture may be placed into a drilled hole 37 in the blunt end of the instrument and the needle pressed or swaged to lock the suture in place. Also, the blunt end of the needle may have an appropriate channel with the suture laid in the channel and the channel crimped or swaged to lock the suture. Extending from the blunt end there is the body portion 33 of the needle. This is the portion that is held by the instrument which is manipulated by the surgeon in placing the suture material. Extending from this blunt end there is the cutting section 31 of the needle or very often termed the blade of the needle. The blade starts at the extreme tip 38 or point of the needle and extends to the maximum width of the needle. The geometric or sectional configuration of the blade will vary depending on the surgical procedure for which the suture is to be used which also determines the number of cutting edges that the blade will have. In this embodiment the point and the entire blade or cutting edges of the needle have been treated to provide a surface hardness over this portion of the needle of at least 50 measured on the Rockwell C Hardness Scale. The body portion of the needle has not been treated to increase its surface hardness but is allowed to remain malleable and ductile so that it is not brittle and does not break when held with great force by the needle holding instrument. Referring to FIGS. 3, 4, and 5 there is shown a sterile surgical needle 40 having a reverse cutting edge 41. Starting at the point 42 of the needle the cross-sectional configuration is triangular with the base of the triangle on the inside of the curve and the apex of the triangle at the outside of the curve. In this embodiment all three of the cutting edges 41, 42, and 43 have been treated to provide them with a surface hardness of 50 or greater on the Rockwell C Hardness Scale. The portion 44 of the needle between cutting edges has not been treated and remains ductile and malleable. This allows the hardened edges to be hardened to an extremely sharp edge while the body and remaining portion of the needle remain malleable.

FIG. 4 is a front view of the needle of FIG. 3 showing the point and the hardened cutting edges.

FIG. 5 shows the triangle cross-section of the body 46 of the needle.

Referring to FIGS. 6, 7, and 8 there is shown another embodiment of a sterile surgical needle according to the presant invention. This needle 50 has three sharp cutting edges 51 which start at the point 52 and proceed along the blade 53 of the needle towards the body 54 of the needle. The entire surface of the needle at the cutting edge or blade section has been surface hardened in accordance with the present invention while the internal center portion of the needle has been allowed to remain malleable and ductile.

The point 52 of the needle is shown in FIG. 7 and the cross-sectional view of the needle at the body portion is shown in FIG. 8. The body portion has been flattened to a shape to aid in holding the needle in an appropriate needle holding instrument. In FIGS. 9, 10 and 11 there is shown another configuration of a sterile surgical needle 60 according to the present invention. This configuration is termed a "spatula" configuration and the body 61 of the needle as more clearly shown in FIG. 11 has a trapezoidal cross-section. The blade 62 or cutting section of the needle comprises a point 63 which expands along the blade to the trapezoidal cross-sectional shape so that it has four cutting edges 64. In this embodiment the point as well as all cutting edges and surfaces 65 extending from the point have been hardened and the edges have two very sharp edges. The cutting edges extending back from surface 65 have also been hardened to sharp edges while the body portion is left untreated and remains ductile.

FIGS. 12, 13 and 14 show a standard taper point or round needle 70. The point portion 71 of the needle has been rendered extra hard by a laser treatment so that the point may be ground to a very sharp point in accordance with the present invention. The needle immediately adjacent the point is the blade section 72. Extending from the "blade" section is the holding section 73 which has a cross-section as shown in FIG. 14. The cross-section of the holding section has been flattened to improve the grip on the needle by a needle holding instrument.

In FIGS. 15, 16, and 17 there is shown a conventional cutting needle 80. The conventional cutting needle has three cutting edges 81 and in this embodiment the edges have been hardened by laser treatment and ground to very sharp cutting edges. The cutting edges extend along the blade 82 of the needle to the holding section 83. As shown in FIG. 17 the holding section of the needle has been flattened to improve stability of the needle in the needle holding instrument.

Figure 18:
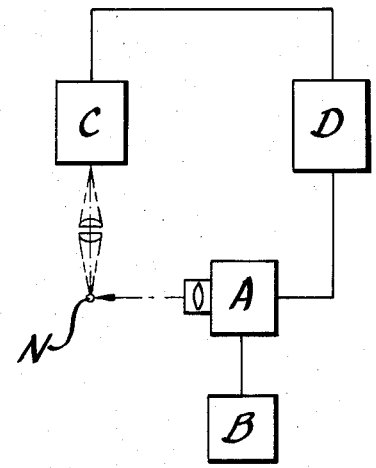
FIG. 18 is a diagram showing the relation between a sterile surgical needle and a laser beam applicator for treating the needle.
Figure 19:
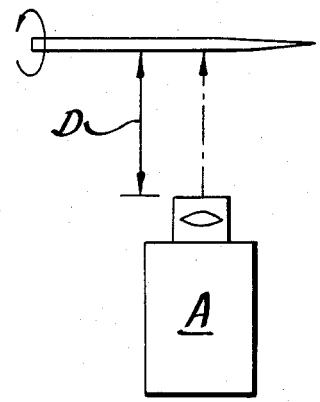
FIG. 19 is an enlarged diagram of a portion of FIG. 18 which depicts the laser beam applicator and a sterile surgical needle being treated in accordance with the present invention.

FIGS. 18 and 19 are schematic diagrams showing one embodiment of a method of treating needles to render the cutting edges of the needle extremely hard in accordance with the present invention. Indicated at (N) is a straight piece of wire which has been mechanically deformed to form the desired pointed end whether it be a tapered point, spatula, etc., as previously described.

(A) is a laser beam applicator which obtains its energy from the laser beam generator (B). At (C) there is shown a monitor or surface inspecting means which continually monitors the surface of the needle and feeds back information on surface characteristics to a control device (D) to control the laser applicator and generator. As is shown in FIG. 19 the needle is rotated in the direction of the arrow at a specified speed. The laser beam produced by the generator (A) is applied to the needle substantially tangentially to the circular path of rotation. During the treatment, the beam is maintained at a constant distance (D) from the needle and is moved along the needle a distance corresponding to the desired length of the cutting edge to be attained. By treating the outer peripheral surface of the needle as described, the needle surface is hardened by the laser beam. In many instances, there may be some burr or flash or other particles on the surface and the needle and the laser beam will melt this material and scatter the metal particles over the hardened surface. The particles may be removed by a gas generator which directs a jet of oxygen or argon or the like is applied to the outer periphery of the treated surface. The depth to which the outer periphery is to be worked and the accuracy of the operation are adjustable by the monitor inspecting means (C) with the results of that inspection fed back to the control means (D). If it is desired not to treat the entire surface of the needle, this may be accomplished by not rotating the needle or by pulsing the laser beam.

Laser beams having power outputs of from about 10 to 150 watts and wave lengths of from about 8 to 12 microns have been found especially suitable for surface hardening of stainless steel needles. A specific laser that may be used is sold by Laakmann Electro-Optics Co. and is identified as an RF-165 $Co_2$ laser.

Needles that may be processed in accordance with the present invention are those made from martensite steels. Such steels are the carbon steels in the 400 series.

Referring to FIG. 20 of the drawings, there is shown a schematic diagram depicting the steps in our new process for producing a very sharp needle. Initially, a straight stainless steel martensite type steel wire is cut to a desired length and one end mechanically deformed (Box D) to produce the desired basic shape to the point of the needle; that is, either a basic taper point, basic spatula point or other point as desired. The pointed wire is treated with a laser beam (Box A) as described in conjunction with FIGS. 18 and 19 and the desired areas treated; that is, either the point, the cutting edges, or the entire cutting surface of the needle may be treated. The desired surface portions of the needle are treated with a laser to develop a hardness as measured on the Rockwell C Scale of at least 45 and preferably 48. The hardened cutting edges are ground by standard grinding techniques to produce very sharp cutting edges (Box Q). The straight needle is shaped into the desired curved surgical needle (Box R); that is, a quarter circle, half circle, etc. Once shaped, the needle is then finished (Box S); that is, it is polished by electro-polishing such as described in U.S. Pat. Nos. 3,701,725 and 3,703,452 or it may be treated by other similar finishing techniques to polish and improve the appearance of the needle. The needle may then have a suture attached to the blunt end as is well known in the art. The needle and suture are packaged and sterilized by techniques also well known in the art.

Although it is preferred to treat the needle while in the straight position, the needle may be first shaped followed by treating the appropriate areas with a laser in accordance with the present invention. The laser techniques require more complicated and complex machinery. The present invention is further illustrated by the following specific example:

EXAMPLE

Keith type cutting edge needle is produced from Type 420 stainless steel using conventional needle making techniques to mechanically form the wire into a cutting edge needle. The size of the wire used is 0.034 inch in diameter. The cutting edges of the needle are treated with a Laakmann RF-165 $CO_2$ laser. The wave length of the laser beam is 10.6 microns. The beam is focused to a spot size having a diameter of approximately 0.008 to 0.010 inch. The laser beam traverses the cutting edge at a rate of 3 inches per minute for a distance of about 0.25 inches from the printed end of the needle. The laser beam is pulsed at a repitition frequency of once every 8 milliseconds with a pulse width of 6 milliseconds. The cutting edge of the needle is hardened to a Rockwell C hardness of $R_c$ 56 to a depth of about 0.003 inch. The edges of the needle are honed to needle sharpness by normal grinding techniques. The cutting edge of the needle has a hardness of $R_c$ 56 while the remainder of the needle remains malleable. A suitable suture material is attached to the blunt end of the needle and the needle and suture sterilized by irridation as is well-known in the art.

While the invention has been described in detail and in accordance with a preferred method of carrying out the process in manufacturing the products, it will be obvious to those skilled in the art after understanding the invention that changes and modifications may be made therein without departing from the spirit and scope of the invention and it is intended in the appended claims to cover such changes and modifications.

What is claimed is;

1. A process for producing a sterile surgical needle having a very sharp cutting edge having a surface hardness of at least 45 measured on the Rockwell C Hardness Scale and a body portion which is malleable and resistant to breaking comprising:
   forming a cutting edge at one end of a piece of steel wire;
   treating said cutting edge with a laser beam having a power output, between 10 watts and 150 watts and a wave length of 8 to 12 microns to harden said edge to a depth of from about 0.0001 inch to 0.010 inch and to a hardness of at least 45 measured on a Rockwell C Hardness Scale;
   sharpening said edge; and
   sterilizing said sharpened steel wire to produce a sterile surgical needle.

2. A process according to claim 1 wherein a suture is swaged into the end of the shaped needle opposite the end at which the cutting edge is formed.

3. A process according to claim 1 or 2 wherein the sharpened needle is shaped to a desired curve prior to sterilization.

4. A process according to claim 3 wherein a point is formed at one end of the steel wire with at least one cutting edge extending from said point.

5. A process according to claim 3 wherein a portion of the wire is formed into a triangular cross-section.

6. A process according to claim 3 wherein a portion of the wire is formed into a trapezoidal cross-section.

* * * * *